United States Patent [19]

Lee

[11] Patent Number: 4,944,849
[45] Date of Patent: Jul. 31, 1990

[54] EXTRACTIVE DISTILLATION OF CYCLOALKANE/ALKANE FEED EMPLOYING SOLVENT MIXTURE

[75] Inventor: Fu Ming Lee, Bartlesville, Okla.

[73] Assignee: Phillips Petroleum Company, Bartlesville, Okla.

[21] Appl. No.: 378,665

[22] Filed: Jul. 12, 1989

[51] Int. Cl.$^5$ ............................................. B01D 3/40
[52] U.S. Cl. ....................... 203/55; 203/56; 203/58; 203/65; 203/69; 585/313; 585/833
[58] Field of Search ............ 203/53, 52, 55, 56, 203/58, 63, 65, 69, 95; 585/856, 313, 833

[56] References Cited

U.S. PATENT DOCUMENTS

| | | | |
|---|---|---|---|
| 2,508,723 | 5/1950 | Mayland et al. | 585/866 |
| 2,679,472 | 5/1954 | Tooke | 203/60 |
| 2,695,322 | 11/1954 | Weedman | 585/839 |
| 2,736,755 | 2/1956 | Reuter et al. | 55/84 |
| 2,771,494 | 11/1956 | Weedman | 585/836 |
| 2,786,804 | 3/1957 | Nelson | 203/60 |
| 2,809,925 | 10/1957 | Nelson | 203/60 |
| 2,839,452 | 6/1958 | Nelson | 203/60 |
| 2,846,485 | 8/1958 | Meason et al. | 585/866 |
| 2,891,894 | 6/1959 | Cier et al. | 203/60 |
| 3,034,969 | 5/1962 | Makin, Jr. | 203/60 |
| 3,114,783 | 12/1963 | Butler et al. | 203/55 |
| 3,431,199 | 3/1969 | Reni et al. | 208/325 |
| 3,992,465 | 11/1976 | Juguin et al. | 585/252 |
| 4,363,704 | 12/1982 | Berg | 203/64 |
| 4,514,262 | 4/1985 | Berg | 203/56 |

OTHER PUBLICATIONS

"Extrachir Distillation Saves Energy", by Ian Sucksmith, Chemical Engineering, Jun. 29, 1987, pp. 91–95.
"Handbook of Separation Techniques for Chem. Engineers," by Philip Schweitzo, McGraw-Hill Book Co., 1979, p. 1-135 to 1-143.
"Perry's Chemical Engineers' Handbook", 6th Edition, McGraw-Hill Book Co., 1984, pp. 13-53 to 13-57.

Primary Examiner—Virginia Manoharan
Attorney, Agent, or Firm—K. K. Brandes

[57] ABSTRACT

A mixture of (a) at least one saturated C5–C9 alcohol (preferably cyclohexanol) and (b) at least one sulfolane (preferably unsubstituted sulfolane, cyclotetramethylene sulfone) is used as solvent in the extractive distillation of a feed mixture of cycloalkane(s) in particular cyclohexane) and close-boiling alkane(s). A novel composition of matter contains (a) and (b), as defined above, and optionally also (c) water.

23 Claims, 1 Drawing Sheet

EXTRACTIVE DISTILLATION OF CYCLOALKANE/ALKANE FEED EMPLOYING SOLVENT MIXTURE

BACKGROUND OF THE INVENTION

In one aspect, this invention relates to the separation of saturated cycloaliphatic hydrocarbons (cycloalkanes, naphthenes) from close-boiling paraffinic hydrocarbons (alkanes, paraffins) by extractive distillation. In another aspect, this invention relates to the use of mixtures of organic compounds as solvent (also referred to as extractant or entrainer) in the aforementioned extractive distillation. In a further aspect, this invention relates to novel mixtures of organic compounds.

Extractive distillation is a well known technique for separating mixtures of components having a relative volatility close to unity (i.e., having nearly equal volatility and having nearly the same boiling point). It is difficult to separate such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, June 28, 1982, pages 91–95, the disclosure of which is herein incorporated by reference. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company, 1984, pages 13-53 to 13-57, the disclosures of which are herein incorporated by reference.

The separation of naphthenes (cycloparaffins), in particular cyclohexane, from close-boiling paraffins by extractive distillation is known and has been described in the patent literature, such as in U.S. Pat. Nos. 2,508,723; 2,771,494; 2,846,485; 2,891,894; 3,034,969 and 4,053,369, the disclosures of which are herein incorporated by reference. However, there is an ever present need to develop more selective solvents than those presently known in the extractive distillation of mixtures of close-boiling paraffins and naphthenes. In particular, it is highly desirable to develop improved extractive distillation processes for producing cyclohexane of high purity, which is a starting material for making nylon and other useful polymeric materials.

SUMMARY OF THE INVENTION

It is an object of this invention to provide a process for separating mixtures of close-boiling naphthenes (cycloalkanes) and paraffins (alkanes) by extractive distillation employing a mixture of organic compounds as solvent. It is another object of this invention to produce cyclohexane of high purity from a mixture comprising cyclohexane and close-boiling isoparaffins (i.e., isoparaffins having nearly the same volatility as cyclohexane) by extractive distillation employing a mixture of organic compounds as solvent. It is a further object of this invention to provide a novel mixture of organic compounds. Other objects and advantages will be apparent from the detailed description of the invention and the appended claims.

In accordance with this invention, in a process for separating at least one cycloalkane (naphthene) containing 5–10 carbon atoms per molecule from at least one close-boiling alkane (paraffin), i.e., one or a plurality of alkanes having nearly the same boiling point at atmospheric pressure conditions as said cycloalkane, by extractive distillation of a feed comprising said at least one cycloalkane and said at least one alkane, the improvement comprises using as solvent (also referred to as extractant or entrainer) a mixture of (preferably consisting essentially of) (a) at least one saturated alcohol selected from the group consisting of alkanols and cycloalkanols (latter preferred), wherein said alcohol contains 5–9 carbon atoms and 1 OH group per molecule, and (b) at least one sulfolane as defined by Formula 1 in U.S. Pat. No. 4,053,369, wherein said sulfolane contains 4–8 carbon atoms per molecule.

In a preferred embodiment, the feed cycloalkane is cyclohexane. In another embodiment, the alcohol component (a) of the solvent is cyclohexanol. In still another preferred embodiment said sulfolane is unsubstituted solfolane, $(CH_2)_4SO_2$, as defined by Formula 4 in U.S. Pat. No. 4,053,369; In a more preferred embodiment, the solvent consists essentially of (a) and (b). In another embodiment, the solvent also comprises 0.1–20 weight-% $H_2O$.

Also in accordance with this invention, a composition of matter is provided which comprises (preferably consists essentially of) a mixture of components (a) and (b), as defined above. Preferably, component (a) is cyclohexanol. Also preferably, component (b) is unsubstituted sulfolane (also referred to as cyclotetramethylene sulfone).

DETAILED DESCRIPTION OF THE INVENTION

Figure 1:
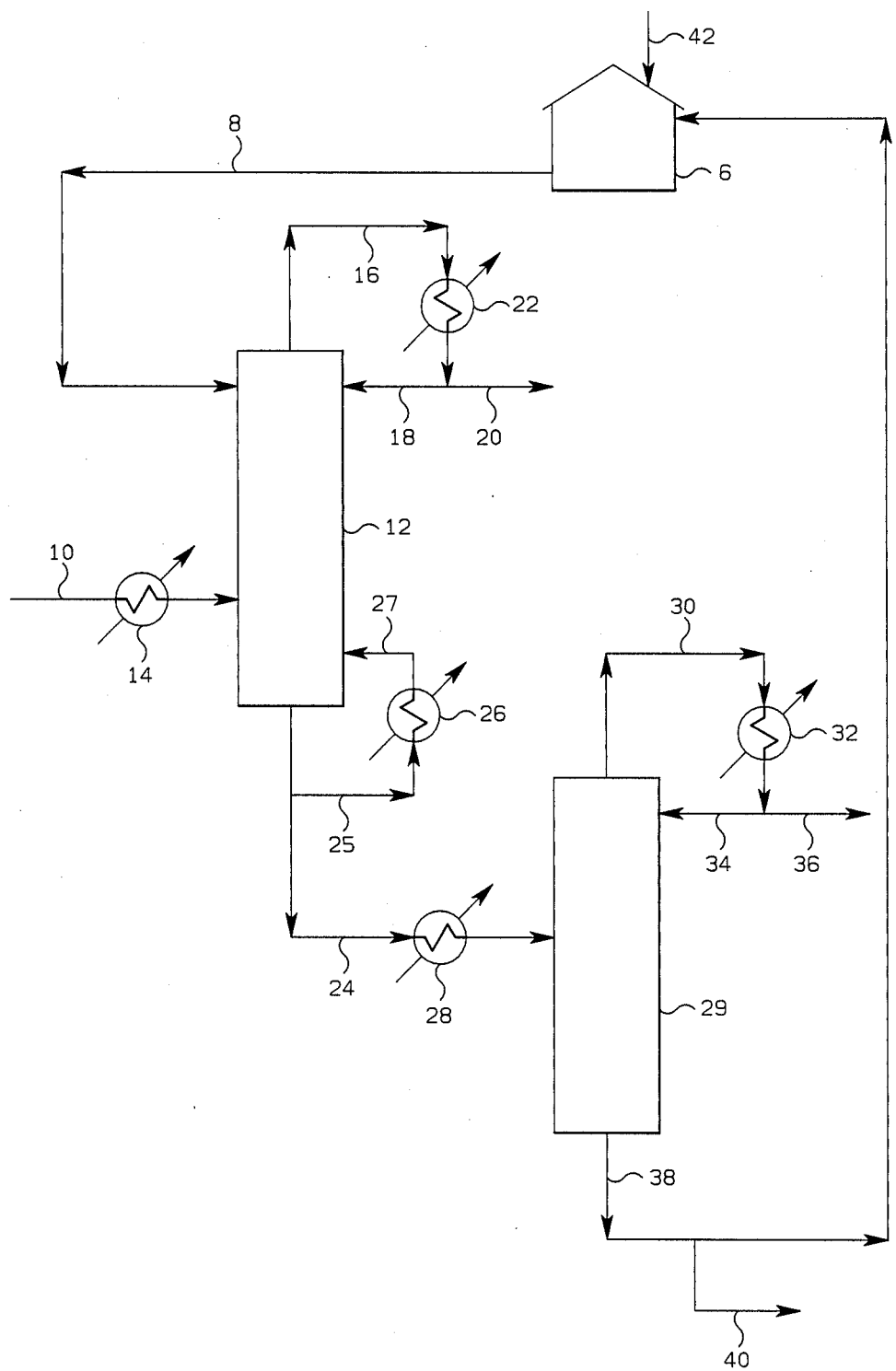
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

Any hydrocarbon feed which contains at least one cycloalkane (naphthene) containing 5–9 carbon atoms per molecule and at least one close-boiling alkane (preferably containing 5–10 carbon atoms per molecule; more preferably branched alkane or isoparaffin) can be used in the process of this invention. Preferably, the boiling point (at atmospheric pressure conditions, i.e., at about 1 atm.) of the cycloalkane(s) and alkane(s) to be separated by extractive distillation is in the range of from about 80° to about 350° F., more preferably about 100°–300° F. Generally, the boiling points of the cycloalkane(s) and the alkane(s) differ by about 0.2°–10° F. (preferably about 0.5°–5° F.), at about 1 atm.

Non-limiting examples of suitable cycloalkanes are cyclopentane, cyclohexane, methylcyclopentane, cycloheptane, 1,1-dimethylcyclopentane, 1,2-dimethylcyclopentane, 1,3-dimethylcyclopentane, ethylcyclopentane, methylcyclohexane, 1,1-dimethylcyclohexane, 1,2-dimethylcyclohexane, 1,3-dimethylcyclohexane, ethylcyclohexane, cycloheptane, cyclooctane, mixtures thereof, and the like. Presently preferred is cyclohexane.

Non-limiting examples of suitable alkanes are n-pentane, n-hexane, 2-methylpentane, 3-methylpentane, n-heptane, 2,2-dimethylpentane, 2,3-dimethylpentane, 2,4-dimethylpentane, 3,3-dimethylpentane, 2-methylhexane, 3-methylhexane, 2,2,3-trimethylbutane, n-octane, 2-methyloctane, n-nonane, mixtures thereof, and the like.

Non-limiting examples of alcohols which are suitable as component (a) of the solvent are cyclopentanol, 2-methylcyclopentanol, 3-methylcyclopentanol, cyclohexanol (preferred), 2-methylcyclohexanol, 3-methylcyclohexanol, 2,3-dimethylcyclohexanol, cycloheptanol, 2-methylcycloheptanol, 3-methylcycloheptanol, 4-methylcycloheptanol, 2,3-dimethylcycloheptanol, n-hexanol, 2-methyl-1-hexanol, 3-methyl-1-hexanol, 3-methyl-2-hexanol, n-heptanol, 2-methyl-1-heptanol, 3-methyl-1-heptanol, 3-methyl-2-heptanol, 2,3-dimethyl-1-heptanol, n-octanol, mixtures thereof, and the like.

Non-limiting examples of sulfolanes which are suitable as component (b) of the solvent are unsubstituted sulfolane (2,3,4,5-tetrahydrothiophene-1,1-dioxide; also referred to as cyclotetramethylene sulfone), 2-methylsulfolane, 3-methylsulfolane, 2,3-dimethylsulfolane, 2,4-dimethylsulfolane, 2-ethylsulfolane, 2,3,4,5-tetramethylsulfolane, and the like, and mixtures thereof. Presently preferred is unsubstituted sulfolane (cyclotetramethylene sulfone).

Any suitable weight ratio of component (b) to component (a) in the solvent (also called extractant of this invention can be employed in the extractive distillation process of this invention. Preferably, the weight ratio of component (b) to component (a) is in the range of from about 0.2:1 to about 30:1, more preferably from about 1:1 to about 10:1. The preferred component (a) is cyclohexanol, and the preferred component (b) is unsubstituted sulfolane. In another preferred embodiment, the solvent further comprises (c) water, preferably about 0.1–20 (more preferably about 0.5–15) weight-% $H_2O$.

Any suitable weight ratio of the solvent to the hydrocarbon containing feed mixture can be employed. Preferably, the solvent to feed weight ratio is in the range of from about 0.5:1 to about 50:1, more preferably from about 3:1 to about 20:1.

Any suitable reflux ratio (i.e., the weight ratio of the portion of condensed vapor which is returned to the distillation column to the portion of condensed vapor which is withdrawn as distillate) can be employed in the process of this invention. Generally, the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally, the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally, the solvent entry location is in the range of from about 50 to about 99 percent of the total height of the packed or trayed column (i.e., within the upper half of the packed column), preferably in the range of from about 70 to about 99 percent, more preferably in the range of from about 80 to about 99 percent.

Any suitable temperature in the distillation vessel (containing primarily the higher boiling feed components and the solvent) can be employed. The temperature is generally in the range of from about 100 to about 400° F., preferably in the range of from about 150 to about 320° F. The extractive distillation column is generally heated (more near the bottom, and less near the top). Generally, the temperature at the top of the column where the vapor exits into the condenser is in the range of from about 100 to about 300° F., preferably in the range of from about 150° to about 250° F. Solvent and feed are generally preheated (generally to a temperature close to the column temperature of the corresponding entry point) before they are introduced into the packed or trayed column. Any suitable pressure can be employed during the extractive distillation. Generally, the pressure is about 5 to about 100 psig, preferably about 8 to about 20 psig.

Generally, the overhead product (withdrawn from the top of the column) contains a smaller volume percentage of cycloalkane (preferably cyclohexane) than the feed and a larger percentage of alkanes (preferably isoalkanes) than the feed. Generally, the bottoms product (a portion of which can be reheated and recycled to the lower portion of the column) contains more of the cycloalkane than the feed, and less of the alkanes (preferably isoalkanes) than the feed. Furthermore, the bottoms product contains substantially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the cycloalkane product, and the like, and can be determined by those having ordinary skills in the art.

The invention can be better understood by reference to FIG. 1 and the following description of a preferred embodiment of the invention. The feed mixture comprising naphthenic and paraffinic hydrocarbons is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in paraffinic hydrocarbons (alkanes) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in paraffinic hydrocarbons and a bottoms stream predominantly comprising the naphthenic hydrocarbons and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising naphthenic hydrocarbons is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., naphthenic compounds (preferably cycloalkane) of high purity (preferably higher than 95%), through conduit 36.

A bottom stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE I

This example demonstrates the superiority as extractant of a mixture of unsubstituted sulfolane (cyclotetramethylene sulfone; hereinafter often referred to as "sulfolane") and cyclohexanol versus each component alone.

To a hydrocarbon mixture of 85 weight percent cyclohexane and 15 weight percent 2,3-dimethylpentane (2,3-DMP) was added an extractive solvent (either the sulfolane or cyclohexanol or a mixture of the above) at a solvent: feed weight ratio of 7:1. The total mixture (including the extractive solvent) was heated under reflux conditions for about 20-30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of 2,3-DMP and cyclohexane in the liquid phase and in the condensed vapor phase were determined. The relative volatility R was calculated as follows:

$$R = \frac{Y1/Y2}{X2/X1} = \frac{Y1/X1}{Y2/X2},$$

wherein Y1 and Y2 are the mole fractions of 2,3-DMP and cyclohexane, respectively, in the vapor phase, and X1 and X2 are the mole fractions of 2,3-DMP and cyclohexane, respectively, in the liquid phase. Test results are summarized in Table I.

TABLE I

| Added Solvent | Relative Volatility R |
| --- | --- |
| Cyclohexanol | 1.04 |
| Sulfolane | 1.07 |
| 50 weight-% Cyclohexanol +50 weight-% Sulfolane | 1.10–1.13 |

Based on the test results in Table I, it is concluded that a mixture of unsubstituted sulfolane and cyclohexanol would be more effective than the sulfolane alone or cyclohexanol alone as solvent in the extractive distillation of cyclohexane and close-boiling paraffins.

EXAMPLE II

This example illustrates the effect of water on the relative volatility of 2,3-DMP and cyclohexane in the presence of a mixture of 50 weight-% cyclohexanol and 50 weight-% unsubstituted sulfolane. The apparatus and feed described in Example I were used for the test series of this example, which was carried out at a 7:1 solvent:feed weight ratio. Test results are summarized in Table II.

TABLE II

| Temp. (°F.) | Wt-% H$_2$O in Liquid Phase | Relative Volatility R |
| --- | --- | --- |
| 224 | 0 | 1.13 |
| 220 | 0.5 | 1.13 |
| 214 | 1.3 | 1.11 |
| 203 | 3.0 | 1.13 |
| 190 | 6.1 | 1.11 |
| 178 | 9.1 | 1.11 |
| 175 | 11.8 | 1.10 |

TABLE II-continued

| Temp. (°F.) | Wt-% H₂O in Liquid Phase | Relative Volatility R |
|---|---|---|
| 172 | 14.3 | 1.11 |

Based on the test results summarized in Table II, it is concluded that the presence of water during the extractive distillation of cyclohexane and close-boiling paraffins with a sulfolane/cyclohexanol solvent would be beneficial in that the boiling temperature (and thus the operating temperature of the extractive distillation process) can be lowered without significantly affecting the relative volatility (i.e., the selectivity).

Reasonable variations, modifications and adaptations for various usages and conditions can be made within the scope of the disclosure and the appended claims, without departing from the scope of this invention.

That which is claimed is:

1. In a process for separating at least one cycloalkane containing 5–10 carbon atoms per molecule from at least one close-boiling alkane by extractive distillation of a feed consisting essentially of said at least one cycloalkane and said at least one alkane, the improvement which comprises employing a solvent consisting essentially of a mixture of
    (a) at least one saturated alcohol selected from the group consisting of alkanols and cycloalkanols, wherein said alcohol contains 5–9 carbon atoms and one OH group per molecule, and
    (b) cyclotetramethylene sulfone;
    wherein said extractive distillation process produces (i) an overhead product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

2. A process in accordance with claim 1, wherein component (a) of said solvent is cyclohexanol.

3. A process in accordance with claim 1, wherein said at least one cycloalkane in said feed is cyclohexane.

4. A process in accordance with claim 1, wherein said at least one cycloalkane in said feed is cyclohexane, and said at least one alkane is at least one isoalkane.

5. A process in accordance with claim 1, wherein the weight ratio of component (b) to component (a) in said solvent is in the range of from about 0.2:1 to about 30:1.

6. A process in accordance with claim 5, wherein said weight ratio of component (b) to component (a) is in the range of from about 1:1 to about 10:1.

7. A process in accordance with claim 1, wherein said at least one cycloalkane in said feed is cyclohexane, component (a) in said solvent is cyclohexanol, and the weight ratio of component (b) to component (a) in said solvent is in the range of from about 0.2:1 to about 30:1.

8. A process in accordance with claim 7, wherein said weight ratio of component (b) to component (a) is in the range of from about 1:1 to about 10:1.

9. A process in accordance with claim 1, wherein the weight ratio of said solvent to said feed is in the range of from about 0.5:1 to about 50:1.

10. A process in accordance with claim 1, wherein said feed boils at a temperature in the range of from about 80° F. to about 350° F., at a pressure of about 1 atm.

11. A process in accordance with claim 1, wherein the boiling point of said at least one cycloalkane and the boiling point of said at least one alkane differ by about 0.2 to about 10° F., at a pressure of about 1 atm.

12. A process in accordance with claim 1, wherein said at least one cycloalkane in said feed is cyclopentane.

13. In a process for separating at least one cycloalkane containing 5–10 carbon atoms per molecule from at least one close-boiling alkane by extractive distillation of a feed consisting essentially of said at least one cycloalkane and said at least one alkane, the improvement which comprises employing solvent consisting essentially of a mixture of
    (a) at least one saturated alcohol selected from the group consisting of alkanols and cycloalkanols, wherein said alcohol contains 5–9 carbon atoms and one OH group per molecule,
    (b) cyclotetramethylene sulfone, and
    (c) about 0.1–20 weight-% water;
    wherein said extractive distillation process produces (i) an overhead product which contains a smaller volume percentage of said at least one cycloalkane and a larger volume percentage of said at least one alkane than said feed, and (ii) a bottoms product which contains said solvent and a larger volume percentage of said at least one cycloalkane and a smaller volume percentage of said at least one alkane than said feed; and wherein said at least one cycloalkane is separated from said solvent and recovered from said bottoms product.

14. A process in accordance with claim 13, wherein component (a) of said solvent is cyclohexanol.

15. A process in accordance with claim 14, wherein said solvent contains about 0.5–15 weight-% water.

16. A process in accordance with claim 13, wherein said at least one cycloalkane in said feed is cyclohexane.

17. A process in accordance with claim 13, wherein said at least one cycloalkane in said feed is cyclopentane.

18. A process in accordance with claim 13, wherein the weight ratio of component (b) to component (a) in said solvent is in the range of from about 0.2:1 to about 30:1.

19. A process in accordance with claim 18, wherein said weight ratio of component (b) to component (a) is in the range of from about 1:1 to about 10:1.

20. A process in accordance with claim 13, wherein component (a) in said solvent is cyclohexanol, and the weight ratio of component (b) to component (a) in said solvent is in the range of from about 0.2:1 to about 30:1.

21. A process in accordance with claim 13, wherein the weight ratio of said solvent to said feed is in the range of from about 0.5:1 to about 50:1.

22. A process in accordance with claim 13, wherein said feed boils at a temperature in the range of from about 80° F. to about 350° F., at a pressure of about 1 atm.

23. A process in accordance with claim 13, wherein the boiling point of said at least one cycloalkane and the boiling point of said at least one alkane differ by about 0.2 to about 10° F., at a pressure of about 1 atm.

* * * * *

UNITED STATES PATENT AND TRADEMARK OFFICE
CERTIFICATE OF CORRECTION

PATENT NO. : 4,944,849
DATED : July 31, 1990
INVENTOR(S) : Fu Ming Lee; Ronald E. Brown It is certified that error appears in the above-identified patent and that said Letters Patent is hereby corrected as shown below:

Title page, item [75] Inventor, delete "," after "Lee" and insert --- ; Ronald E. Brown, both of --- therefor.

Claim 13, Column 8, Line 17, insert --- a --- after "employing".

Signed and Sealed this

Twenty-fifth Day of February, 1992

Attest:

HARRY F. MANBECK, JR.

*Attesting Officer*     *Commissioner of Patents and Trademarks*